US012685526B2

(12) United States Patent
Woodward

(10) Patent No.: US 12,685,526 B2
(45) Date of Patent: Jul. 21, 2026

(54) SUTURING TOOL AND GRASPING TOOL

(71) Applicant: TTP Plc., Royston (GB)

(72) Inventor: Adrian Woodward, Royston (GB)

(73) Assignee: TTP Plc., Royston (GB)

( * ) Notice: Subject to any disclaimer, the term of this patent is extended or adjusted under 35 U.S.C. 154(b) by 103 days.

(21) Appl. No.: 18/570,143

(22) PCT Filed: Jun. 15, 2022

(86) PCT No.: PCT/GB2022/051509
§ 371 (c)(1),
(2) Date: Dec. 14, 2023

(87) PCT Pub. No.: WO2022/263822
PCT Pub. Date: Dec. 22, 2022

(65) Prior Publication Data
US 2024/0260958 A1 Aug. 8, 2024

(30) Foreign Application Priority Data

Jun. 15, 2021 (GB) ...................................... 2108521
Jun. 15, 2021 (GB) ...................................... 2108545

(51) Int. Cl.
*A61B 17/04* (2006.01)
*A61B 17/06* (2006.01)
*A61B 17/062* (2006.01)

(52) U.S. Cl.
CPC .... *A61B 17/0469* (2013.01); *A61B 17/06061* (2013.01); *A61B 17/0625* (2013.01)

(58) Field of Classification Search
CPC .......... A61B 17/0469; A61B 17/06061; A61B 17/0625
See application file for complete search history.

(56) References Cited

U.S. PATENT DOCUMENTS 5,674,230 A * 10/1997 Tovey ................ A61B 17/0469
606/139
5,814,054 A * 9/1998 Kortenbach ......... A61B 17/062
606/147

(Continued)

FOREIGN PATENT DOCUMENTS

WO 2019/117811 A1 6/2019

OTHER PUBLICATIONS

PCT Patent Application PCT/GB2022/051509 International Search Report and Written Opinion dated Nov. 17, 2022.

*Primary Examiner* — Phong Son H Dang
(74) *Attorney, Agent, or Firm* — Erise IP, P.A.

(57) ABSTRACT

A suturing tool for an endoscope or a laparoscope, the tool comprising: a symmetric suturing needle comprising a point at each end of the needle; and a pair of jaws for suturing a target object between the jaws, each jaw comprising a needle holder for holding the suturing needle, the pair of jaws being configured to move between an open jaw position and a closed jaw position, wherein each needle holder comprises a moveable locking element configured to move between a closed lock position in which the suturing needle is held by the needle holder and an open lock position at which the suturing needle is released by the needle holder, and each needle holder further comprises a resilient control mechanism configured to switch the locking element between the closed lock position and the open lock position.

9 Claims, 13 Drawing Sheets

(56)  References Cited

U.S. PATENT DOCUMENTS

| | | | |
|---|---|---|---|
| 5,908,428 A * | 6/1999 | Scirica | A61B 17/0625 |
| | | | 221/113 |
| 8,628,545 B2 * | 1/2014 | Cabrera | A61B 17/00234 |
| | | | 606/144 |
| 8,747,424 B2 * | 6/2014 | Taylor | A61B 17/04 |
| | | | 606/144 |
| 2006/0036232 A1 * | 2/2006 | Primavera | A61B 17/29 |
| | | | 604/411 |
| 2012/0150197 A1 * | 6/2012 | Malkowski | A61B 17/0625 |
| | | | 606/144 |
| 2017/0071601 A1 | 3/2017 | Park et al. | |
| 2017/0340320 A1 * | 11/2017 | Baril | A61B 17/00234 |
| 2019/0059881 A1 | 2/2019 | Vrancken Peeters | |
| 2019/0183484 A1 * | 6/2019 | Malkowski | A61B 17/0491 |
| 2020/0038012 A1 * | 2/2020 | Nicholas | A61B 17/0625 |

* cited by examiner

SUTURING TOOL AND GRASPING TOOL

RELATED APPLICATIONS

The present application is a national stage application under 35 U.S.C. § 371 of International Application No. PCT/GB2022/051509, filed Jun. 15, 2022, which claims priority to Great Britain Patent Application Nos. 2108545.1 filed Jun. 15, 2021, and 2108521.2 filed Jun. 15, 2021. The above referenced applications are hereby incorporated by reference.

TECHNICAL FIELD

The disclosure relates to grasping tools and suturing tools for keyhole-type surgery such as endoscopic surgery or laparoscopic surgery. In keyhole-type surgery, a tool for grasping and/or suturing may be arranged at the distal end of a long probe and operated from a proximal end of the probe via one or more tendons. The tool may for example be used to manipulate native tissue or to operate a suture needle.

BACKGROUND

FIGS. 1A and 1B are a side view and a perspective view schematically illustrating a known grasping tool 1.

In FIG. 1A, the grasping tool 1 comprises a support 11, a fixed jaw 12 and a moveable jaw 13AB.

The support 11 is a base portion which may be connectable to the long probe of, for example, an endoscope or laparoscope. As a result, the probe can control an overall position of the grasping tool.

Each of the fixed jaw 12 and moveable jaw 13AB is secured to the support 11 at a backward end and has a forward end extending from the support for grasping a target object between the jaws, where the target object may for example be native tissue of a patient or may be a secondary tool manipulated by the grasping tool, such as a suturing needle.

The fixed jaw 12 of this example has a fixed position relative to the support 11.

The moveable jaw 13AB is connected to the support 11 via a hinge 14, and is operable to rotate on the hinge 14 to open and close the pair of jaws 12, 13AB.

The grasping tool is controlled using a tendon bundle (i.e. one or more tendons) that extend between the proximal and distal ends of the probe.

Specifically, the moveable jaw 13AB is controlled using two tendons 15A and 15B, one tendon 15A for closing the pair of jaws and one tendon 15B for opening the pair of jaws. Specifically, the two tendons 15A and 15B connected via a pulley loop 151AB that extends around a pulley surface of the hinge 14. Tension is applied to the tendon 15A or the tendon 15B in order to apply a closing force or an opening force on the moveable jaw 13AB.

In the configuration of FIG. 1A, a closing force F of the pair of jaws depends on the tension T in the tendons, the radius R of pulley surface of the hinge, and the length L of the jaws. These lengths and forces are labelled in FIG. 1A.

FIG. 1B differs from FIG. 1A in that the fixed jaw 12 is replaced with a second moveable jaw 13CD. The second moveable jaw 13CD is operated similarly to the first moveable jaw 13AB, and two additional tendons 15C, 15D are provided to operate the second moveable jaw 13CD using a second pulley loop 151CD that extends around a second pulley surface of the hinge 14.

With the configuration of FIG. 1B, a tendon bundle comprising four tendons is required to provide a pair of jaws which can open and close, and which can be reoriented to direct the pair of jaws away from an axis of a distal end of the long probe.

It is desirable to reduce the number of tendons required to provide the grasping tool. The tendons take up space in a typically narrow internal channel connecting the proximal and distal ends of the probe, and only a small number of tendons can be provided for all of the possible functions which may need to be controlled from the proximal end of the probe. As a result, a reduction of tendons required for the grasping tool can enable provision of other tendon-controlled functions in the probe.

Additionally, it is desirable to increase the maximum closing force of the pair of jaws, so that the grasping tool can perform a greater variety of functions.

On the other hand, suturing requires passing a needle and thread through native tissue multiple times. In prior art systems, this has been achieved by passing a needle back and forth between two opposing jaws which are arranged at the distal end of a long probe (for example an endoscope or laparoscope), these jaws being similar to the previously described grasping tool. The jaws open to enable use of the needle for suturing, and close to enable passing the needle between the jaws. This requires a way of attaching and detaching the needle from each jaw.

In a particular prior art system described in WO 2019/117811 A1, this was achieved using a moveable locking element 271 in the jaw 23 that is configured to engage with the suture needle 3, as shown in FIG. 2A (which corresponds to part of FIG. 1D of WO 2019/117811 A1).

As shown in FIG. 2B (which corresponds to part of FIG. 7A in WO 2019/117811 A1), one locking element 271 per jaw was controlled using a needle control tendon system 28 extending around pulleys.

It is desirable to provide alternative, and preferably simplified, ways of manipulating a suture needle.

Specifically, in long probe systems such as endoscopes and laparoscopes, tendons are used for different purposes to control the probe from a proximal end. However, an internal channel of the long probe typically has limited capacity for tendons, and therefore it is desirable to reduce the required number of tendons.

Additionally, in prior art suturing tools, the pair of jaws can only be moved in limited ways in order to direct the suturing needle. It is desirable to provide a suturing tool which can be directed with a fuller range of motion relative to the distal end of an endoscope or laparoscope system.

SUMMARY

According to a first aspect, the present disclosure provides a suturing tool for an endoscope, the tool comprising: a symmetric suturing needle comprising a point at each end of the needle; and a pair of jaws for suturing a target object between the jaws, each jaw comprising a needle holder for holding the suturing needle, the pair of jaws being configured to move between an open jaw position and a closed jaw position, wherein each needle holder comprises a moveable locking element configured to move between a closed lock position in which the suturing needle is held by the needle holder and an open lock position at which the suturing needle is released by the needle holder, and each needle holder further comprises a resilient control mechanism configured to switch the locking element between the closed lock position and the open lock position.

By including a resilient control mechanism, the locking element can be configured with a default position (either the open lock position or the closed position) to which it will return without being driven by a tendon. Referring to FIG. 2B, this can reduce the required number of tendon ends required to run along the long probe of an endoscope or laparoscope.

Optionally, the jaws have opposite configurations of the control mechanism such that, when the locking element of one jaw is in the open lock position, the locking element of the other jaw is in the closed lock position. With this configuration, the needle can switch between being held by one jaw and being held by the other jaw, without being locked to both jaws or released completely from the jaws.

Optionally, the suturing needle comprises an engagement element adjacent to each end, the engagement element being adapted to engage with the locking element of a needle holder. By adapting the needle as well as the jaws, the needle can be more securely held by the suturing tool.

Optionally, the control mechanism comprises a biasing element configured to bias the locking element toward one of the closed lock position and the open lock position, and a needle control tendon configured to move the locking element to the other of the closed lock position and the open lock position. By using a biasing/tendon pair, the complexity of the tendon system can be reduced to pulling only for controlling the needle holder of a jaw.

Optionally, the control mechanism comprises a bistable latch mechanism configured to alternately switch the locking element between the open lock position and the closed lock position, and a latch trigger for triggering the latch mechanism. By including a bistable latch mechanism, the needle holder can be controlled in both a closed lock position and an open lock position without maintaining tension in a tendon.

Optionally, the latch trigger is a needle control tendon.

Optionally, the latch trigger is a pressure trigger configured to respond to a pressure applied to the needle by the pair of jaws. By using a pressure trigger, needle control tendons are not required at all for passing the needle back and forth between the jaws.

Optionally, the control mechanism comprises a needle control tendon that has a split distal end connected to the locking elements, and has a single proximal end. With this configuration, the control mechanism can be operated using tendons, but only one tendon is required to extend along a long probe for control at the proximal end of the probe.

Optionally, the control mechanism comprises a needle control tendon that is also a jaw control tendon configured to move the pair of jaws between the open jaw position and the closed jaw position. By combining needle control tendon functionality with jaw control tendon functionality, the total number of tendons can be reduced.

According to a second aspect, the present disclosure provides an endoscope or a laparoscope comprising a suturing tool according to the first aspect, wherein the suturing tool is attached to a distal end of the endoscope and the suturing tool is controlled via the endoscope.

According to a third aspect, the present disclosure provides an endoscope or a laparoscope comprising an elongate body having an internal storage channel and a suturing tool according to the first aspect in the internal storage channel, the endoscope or laparoscope being configured to deploy the suturing tool at a distal end of the elongate body.

According to a fourth aspect, there is provided a grasping or suturing tool for an endoscope, the tool comprising: a support for positioning the tool; a pair of jaws, each jaw being secured to the support at a backward end and having a forward end extending from the support for grasping or suturing a target object between the jaws, the pair of jaws being configured to move between an open position and a closed position; one or more biasing elements configured to bias the pair of jaws to a first position, wherein the first position is one of the open position and the closed position; a jaw control tendon bundle configured to move the pair of jaws to a second position when the jaw control tendon bundle is tensioned, wherein the second position is the other of the open position and the closed position.

The open position is a position at which there is significant space between the jaws. The closed position is a position at which the jaws are close together. The magnitude of the difference between the open and closed positions is configured according to a chosen application of the grasping tool.

The inclusion of a biasing element means that only one tendon is required to move the pair of jaws between the open position and the closed position. In one case, the biasing element biases the pair of jaws to the open position, and applying tension to the jaw control tendon bundle moves the pair of jaws to the closed position and releasing the jaw control tendon bundle moves the pair of jaws to the open position. In another case, the biasing element biases the pair of jaws to the closed position, and applying tension to the jaw control tendon bundle moves the pair of jaws to the open position and releasing the jaw control tendon bundle moves the pair of jaws to the closed position.

Optionally, the pair of jaws are secured to the support via a hinge, and the jaw control tendon bundle comprises a pair of jaw control tendons, wherein each of the jaw control tendons is configured to rotate the pair of jaws in a respective direction around the hinge, when the jaw control tendon is tensioned individually. The biasing element means that, when only a part of the jaw control tendon bundle is tensioned, the pair of jaws remain in the first position relative to each other (closed or open), but an orientation of the pair of jaws as a whole rotates around the hinge.

Optionally: the first position is the open position and the second position is the closed position; each of the pair of jaws comprises a first anchor or pivot arranged between the forward end and the backward end, and a second pivot arranged between the forward end and the backward end, and the jaw control tendon bundle comprises a pair of tendons, each of which extends from the first anchor or pivot of one jaw, around the second pivot of the other jaw, and then through the support to a control end of the tendon. This configuration means that the closing force of the pair of jaws is limited by the positions of the first anchor or pivot and the second pivot, and is no longer limited by the radius of the hinge.

Optionally: each of the pair of jaws comprises a third pivot arranged between the forward end and the backward end; and between extending around the second pivot of the other jaw, and extending through the support to a control end of the tendon, each of the pair of tendons extends around the third pivot of the one jaw. This configuration decreases the ratio of a movement between the pair of jaws to a movement of the tendons between the jaws, and thus increases the closing force of the pair of jaws.

Optionally, the one or more biasing elements comprise resilient bending portions of the jaws. Resilient bending portions provide a simple configuration of the biasing elements.

Optionally, the resilient bending portions comprise a spring element connecting the jaws together. A spring element provides a simple configuration for a biasing element which can be combined with known jaws.

Optionally, the one or more biasing elements comprise a torsion spring having a centre which is offset from a joint between the pair of jaws. By offsetting the centre of the torsion spring, the direction of a force provided by the biasing element changes as the pair of jaws opens or closes.

According to a fifth aspect, there is provided an endoscope or a laparoscope comprising a tool according to the fourth aspect, wherein the support is attached to a distal end of the endoscope and the tendons are controlled via the endoscope.

According to a sixth aspect, there is provided an endoscope or a laparoscope comprising an elongate body having an internal storage channel and a tool according to the fourth aspect in the internal storage channel, the endoscope or laparoscope being configured to deploy the tool at a distal end of the elongate body.

BRIEF DESCRIPTION OF THE DRAWINGS

Embodiments of the invention will now be described by reference to the following drawings.

DETAILED DESCRIPTION

Figure 3C:
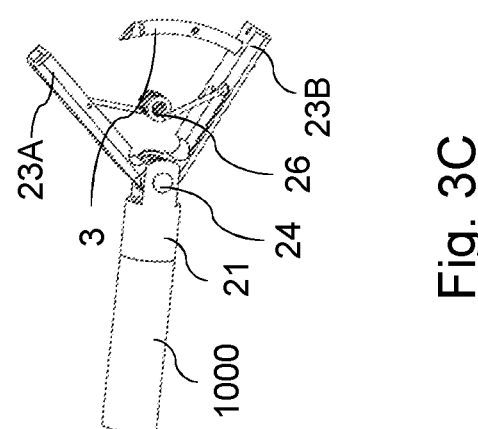
FIGS. 3A to 3C are schematic perspective illustrations of a suturing tool according to the invention.
Figure 3B:
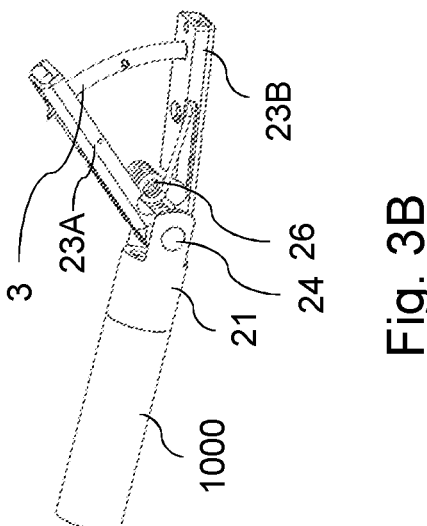
Figure 3A:
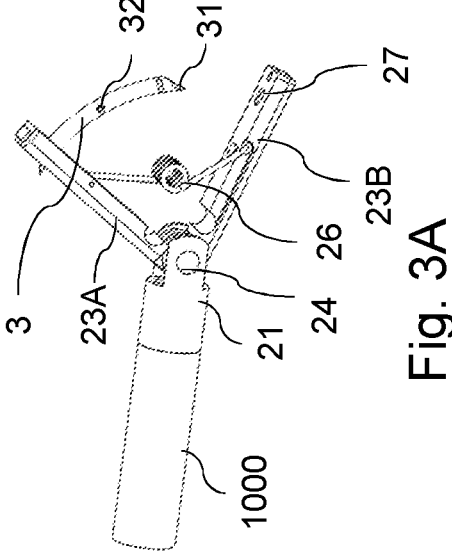

FIGS. 3A to 3C are schematic perspective illustrations of a suturing tool according to the invention. FIGS. 3A to 3C illustrate a motion of the suturing tool as a needle 3 is transferred between a pair of jaws 23A, 23B of the suturing tool, for suturing a target object between the jaws, such as a seam in native tissue which is to be sutured.

The needle 3 is a symmetric suturing needle comprising a point 31 at each end of the needle. This means that both end of the needle can be used for suturing, and suturing along a seam can be achieved by passing the needle 3 back and forth through the seam between the jaws 23A, 23B, without rotating the needle or moving the jaws away from the seam. Additionally, the needle 3 is connected to a suturing thread which is drawn through the target object with the needle. The suturing thread may for example extend through a needle eye 32.

Initially, as shown in FIG. 3A, the suturing needle 3 is held by a first jaw 23A, and the pair of jaws is in an open jaw position. In this position, the needle 3 can be aligned to pass through the target object starting at its free point opposite to the first jaw 23A.

The pair of jaws then moves to a closed jaw position, as shown in FIG. 3B. In the closed jaw position, one end of the needle 3 is located in a needle holder 27 of the first jaw 23A, and the other end of the needle 3 is located in a needle holder 27 of the second jaw 23B. At this point, the needle holder 27 of the first jaw 23A releases the needle 3 and the needle holder 27 of the second jaw 23B holds the needle 3.

Subsequently, the pair of jaws moves to the open jaw position, as shown in FIG. 3C. Since the needle 3 is no longer held by the first jaw 23A, the needle can pass fully through a target object and be relocated to pass through the target object again for a next portion of a suture.

In this example, a backward end of each of the jaws 23A, 23B is connected to a support 21 via a hinge 24. The jaws 23A, 23B are controlled to pivot around the hinge 24 in order to move between the open jaw position (FIGS. 3A, 3C) and the closed jaw position (FIG. 3B).

The support 21 provides a base portion which may be connectable to the distal end of a long probe 1000 (such as an endoscope or laparoscope). As a result, the probe can control an overall position of the suturing tool.

Additionally, in this example, a jaw biasing element 26 is arranged between the pair of jaws. The jaw biasing element 26 is discussed further below with respect to FIGS. 10A to 10D.

Figure 4B:
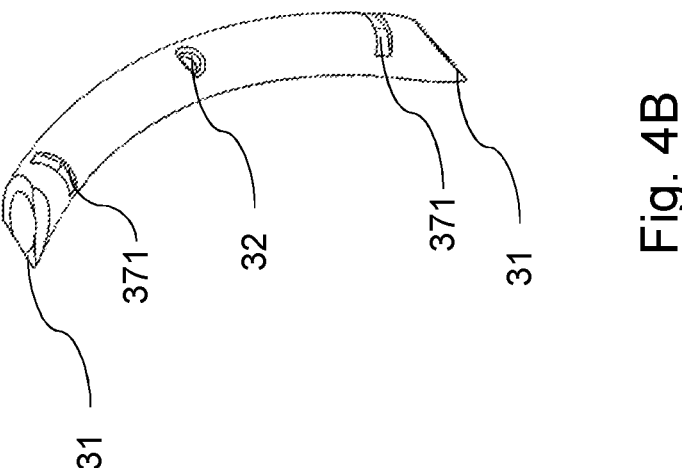
FIGS. 4A and 4B are schematic illustrations of a first needle holder mechanism of the suturing tool.
Figure 4A:
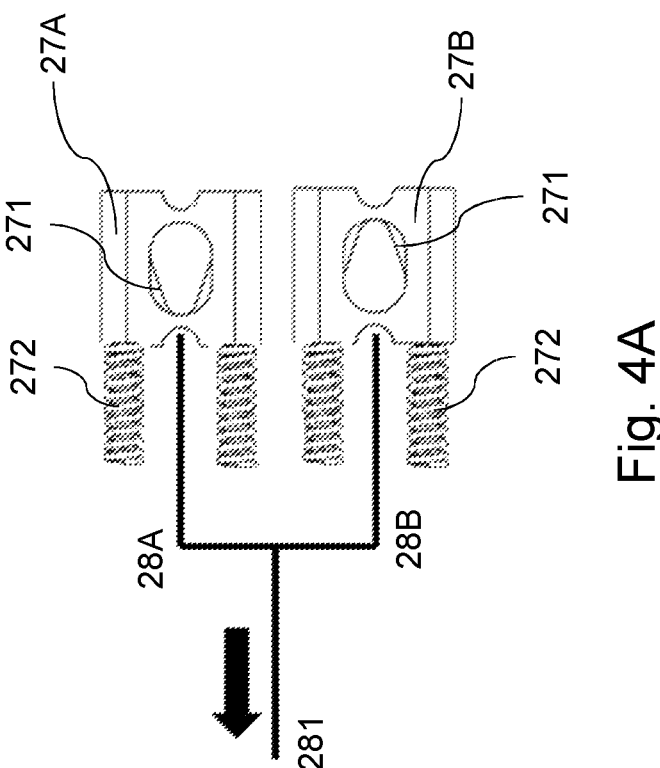

FIGS. 4A and 4B are schematic illustrations of a first example of a needle holder mechanism of the suturing tool. Specifically, FIG. 4A illustrates features of a needle holder 27A, 27B and needle control tendon 28A, 28B of each jaw 23A, 23B. FIG. 4B illustrates corresponding features of a needle 3.

Referring to FIGS. 4A and 4B, in this first example, each needle holder comprises a moveable locking element 271, and the suturing needle 3 comprises an engagement element 371 adjacent to each end of the needle. When the locking element 271 is in a closed lock position, the locking element 271 of one jaw can interfere with an engagement element 371, and hold an associated end of the needle in the needle holder (as illustrated in FIGS. 3A and 3C). On the other hand, when the locking element 271 is in an open lock position, the needle holder allows the needle end to pass in and out of the needle holder.

The locking element 271 and engagement element 371 may for example be any combination of protrusions and recesses configured to fit together in the closed lock position. In some embodiments, the engagement element 371 may be omitted and the needle 3 may be held by friction using the locking element 271 in the needle holder 27. In other embodiments, the needle 3 may comprise a moving part of the needle holding mechanism, such as a biasing element configured to push the locking element 271 away from the closed lock position.

Additionally, each needle holder comprises a resilient control mechanism for switching the moveable locking element 271 between the closed lock position and the open lock position, and vice versa. In the first example, the resilient control mechanism comprises a lock biasing element 272 and a needle control tendon 28A, 28B.

The needle control tendon 28A, 28B is configured to move the locking element towards one of the closed lock position and the open lock position. The needle control tendon 28A, 28B is to be connected to the proximal end of a long probe 1000 so that tension can be applied or relaxed to control the locking element 271.

The lock biasing element 272 is configured to bias the locking element 271 towards the other one of the closed lock position and the open lock position. The lock biasing element 272 may, for example, comprise a spring configured to provide a force in a direction opposite to that of tension in the needle control tendon 28A, 28B.

With this configuration, tensioning the needle control tendon 28A, 28B moves the locking element 271 to a first position and, when the needle control tendon 28A, 28B is relaxed, the lock biasing element 272 moves the locking element 271 to a second position. The first and second positions may be the open lock position and closed lock position, or vice versa.

Preferably the jaws have opposite configurations of the resilient control mechanism such that, when both needle control tendons 28A, 28B are tensioned, the locking element 271 of one jaw 23A is in the closed lock position while the locking element 271 of the other jaw 23B is in the open lock position. Similarly, when both needle control tendons 28A, 28B are relaxed, the locking element of the one jaw 23A is in the open lock position while the locking element 271 of the other jaw 23B is in the closed lock position. Since the suturing tool passes the needle 3 back and forth between the jaws, this configuration means that the needle control tendons 28A, 28B of each jaw can be joined together, and the needle holders can be controlled using only one common needle control tendon 281 that extends along the probe 1000.

Figure 5B:
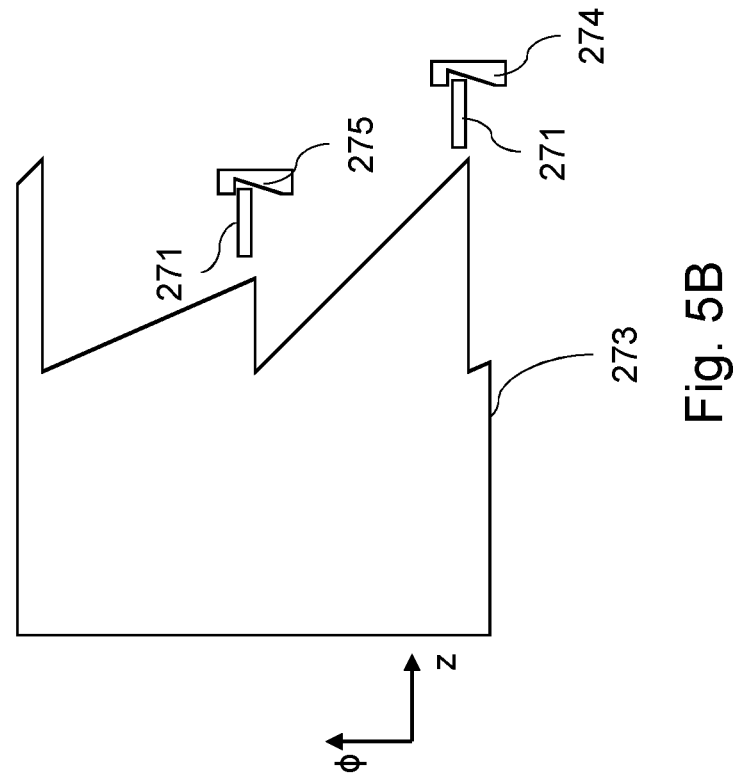
FIGS. 5A and 5B are schematic illustrations of a second needle holder mechanism for the suturing tool.
Figure 5A:
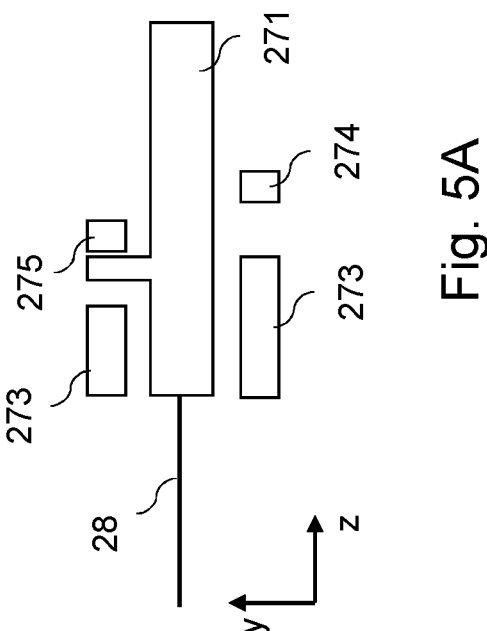

FIGS. 5A and 5B are schematic illustrations of a second example of a needle holder mechanism of the suturing tool. In this case, a mechanism for only one jaw is illustrated, although the mechanism may be the same in both jaws 23A, 23B. The needle 3 may be similar in this example to the needle described above for the first example.

In the second example, the needle holder mechanism comprises a bistable latch mechanism configured to alternately switch the locking element 271 between the open lock position and the closed lock position, and a latch trigger for triggering the latch mechanism.

The needle holder mechanism may have a generally cylindrical configuration, where the locking element 271 moves back and forth along a labelled z direction between the open lock position and the closed lock position. FIG. 5A is a cross-section through the cylindrical configuration, while FIG. 5B is a flattened view of a perimeter of the cylindrical configuration. As shown in FIG. 5B, the perimeter forms a closed loop with the top of the illustration wrapping around to the bottom of the illustration.

In this case, the latch trigger is a needle control tendon 28 (i.e. 28A or 28B) similar to the first example. However, in the second example, the needle control tendon 28 is tensioned to switch between the open lock position and the closed lock position, but does not need to be tensioned in either stable position.

In addition to a biasing element (not shown), the bistable latch mechanism comprises a guide track 273, a closed lock notch 274 and an open lock notch 275. The guide track 273 may for example take the form of a hollow drum. The guide track 273 is configured to guide a surface feature of the locking element 271 back and forth between the closed lock notch 274 and the open lock notch 275.

In the example shown in FIG. 5B, when the locking element 271 starts in the closed lock position adjacent to closed lock notch 274 and is pulled in a negative z direction by tension in the needle control tendon 28, the guide track 273 guides the locking element 271 to rotate in a labelled φ direction and align with the open lock notch 275. When the needle control tendon 28 is relaxed, the biasing element biases the locking element 271 in the positive z direction to engage with the open lock notch 275 in the open lock position.

Similarly, when the locking element 271 starts in the open lock position adjacent to open lock notch 275 and is pulled in a negative z direction by tension in the needle control tendon 28, the guide track 273 guides the locking element 271 to rotate in a labelled φ direction (wrapping around from the top to the bottom of the illustrated flattened loop) and align with the closed lock notch 274. When the needle control tendon 28 is relaxed, the biasing element biases the locking element 271 in the positive z direction to engage with the closed lock notch 274 in the closed lock position.

This configuration of a bistable latch mechanism is just one example to illustrate the principle and many other configurations are possible. Similar configurations are known, for example, in retractable pens.

In one example, the guide track 273 is free to rotate around the locking element 271. In other words the guide track 273, closed lock notch 274 and open lock notch 275 rotate in the negative φ direction, and the locking element 271 does not need to rotate.

In another example, instead of a cylindrical configuration, the bistable latch mechanism may have a guide track with two parallel linear portions with one guiding the locking element from the closed lock position to the open lock position and the other guiding the locking element from the open lock position to the closed lock position.

Figure 6:
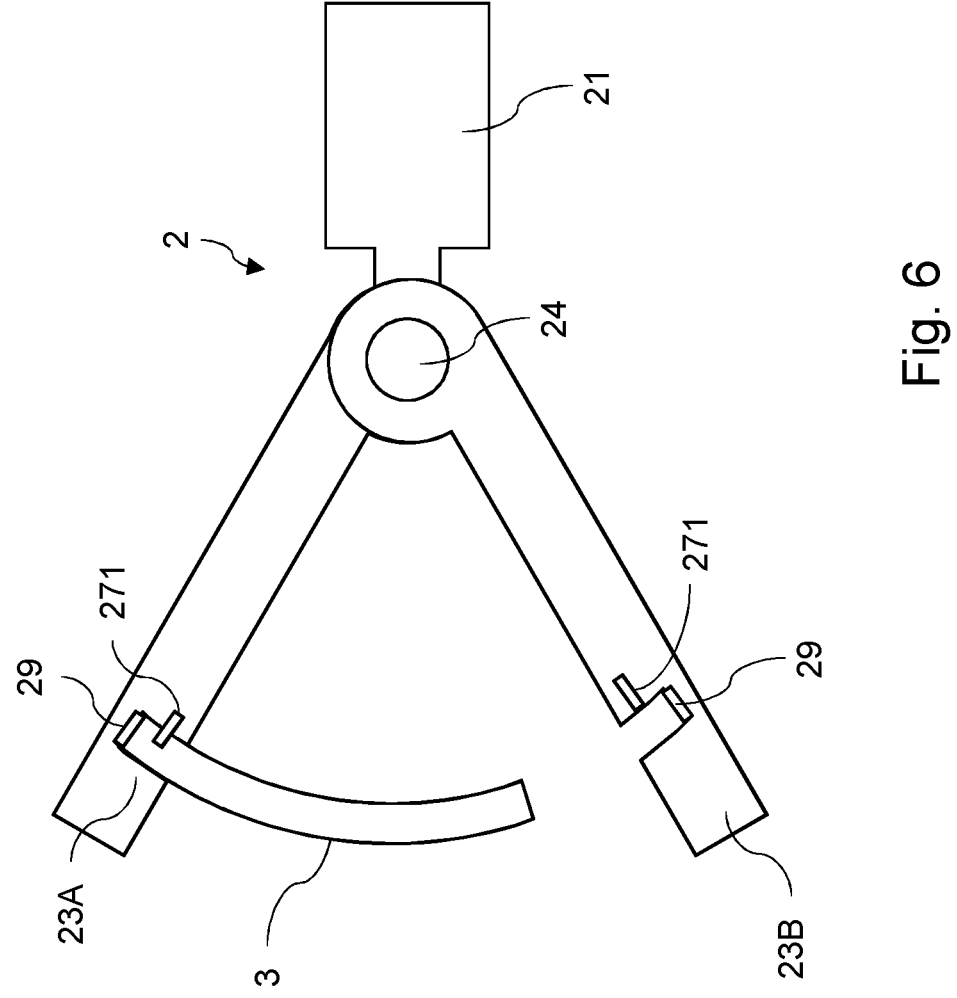
FIG. 6 is a schematic illustration of further optional features for a needle holder mechanism for the suturing tool.

FIG. 6 is a schematic illustration of further optional features for a needle holder mechanism for the suturing tool. Specifically, in this example, the latch trigger of for a bistable latch mechanism is a pressure trigger 29 arranged in each jaw 23A, 23B and configured to respond to a pressure applied to the needle 3 by the pair of jaws 23A, 23B.

When the jaws are moved to a closed jaw position, the pressure trigger 29 in each jaw is squeezed between the jaw and each end of the needle 3. This can be used to trigger the bistable mechanism in each jaw, and switch the jaw that is currently holding the needle 3 (as in the switch which occurs in a position shown in FIG. 3B, between the positions shown in FIGS. 3A and 3C). With such a pressure trigger 29, the needle control tendons 28 may be entirely unnecessary for passing the needle 3 between the jaws 23A, 23B. One or both of the needle control tendons 28A, 28B may nevertheless be included in order to release and remove the needle before retracting the suturing tool from a patient.

Other latch triggers for the bistable latch mechanism are possible. For example, the bistable latch mechanism could be triggered by detecting a position of the needle relative to the respective jaw.

Figure 7A:
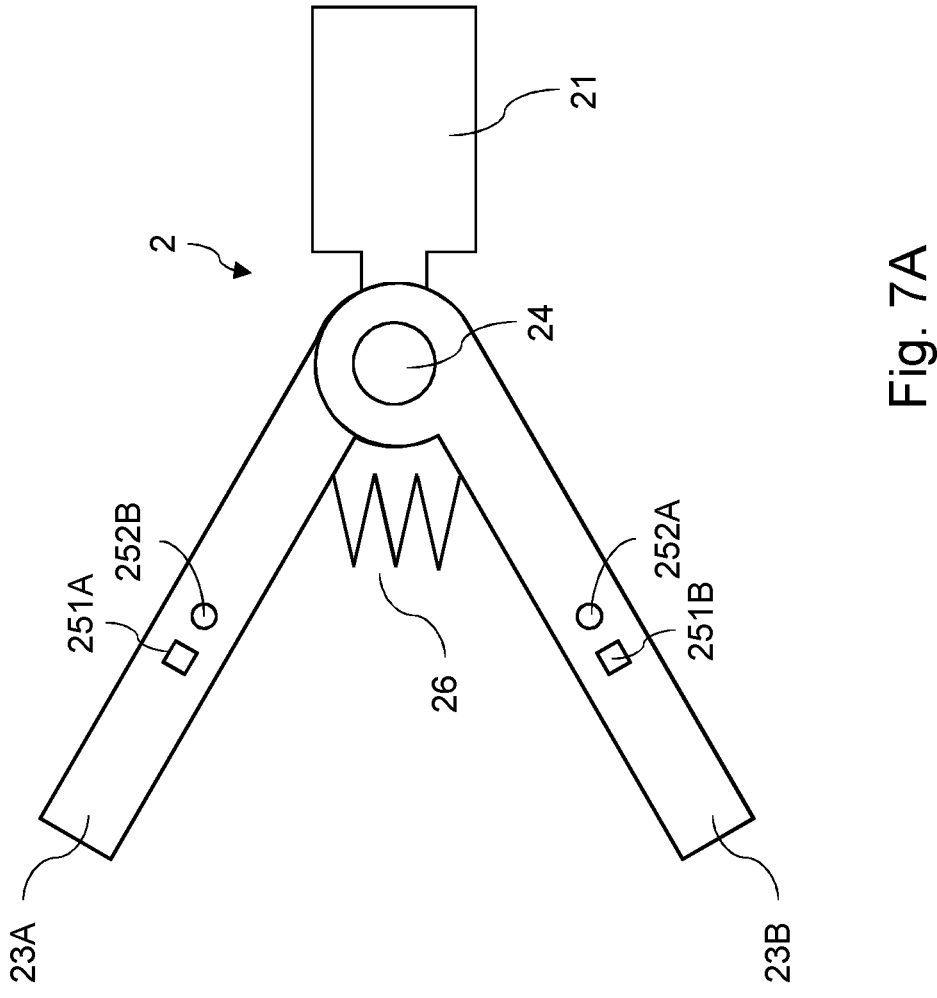
FIGS. 7A and 7B are schematic illustrations of a mechanism for controlling the jaws of the suturing tool or a grasping tool.
Figure 7B:
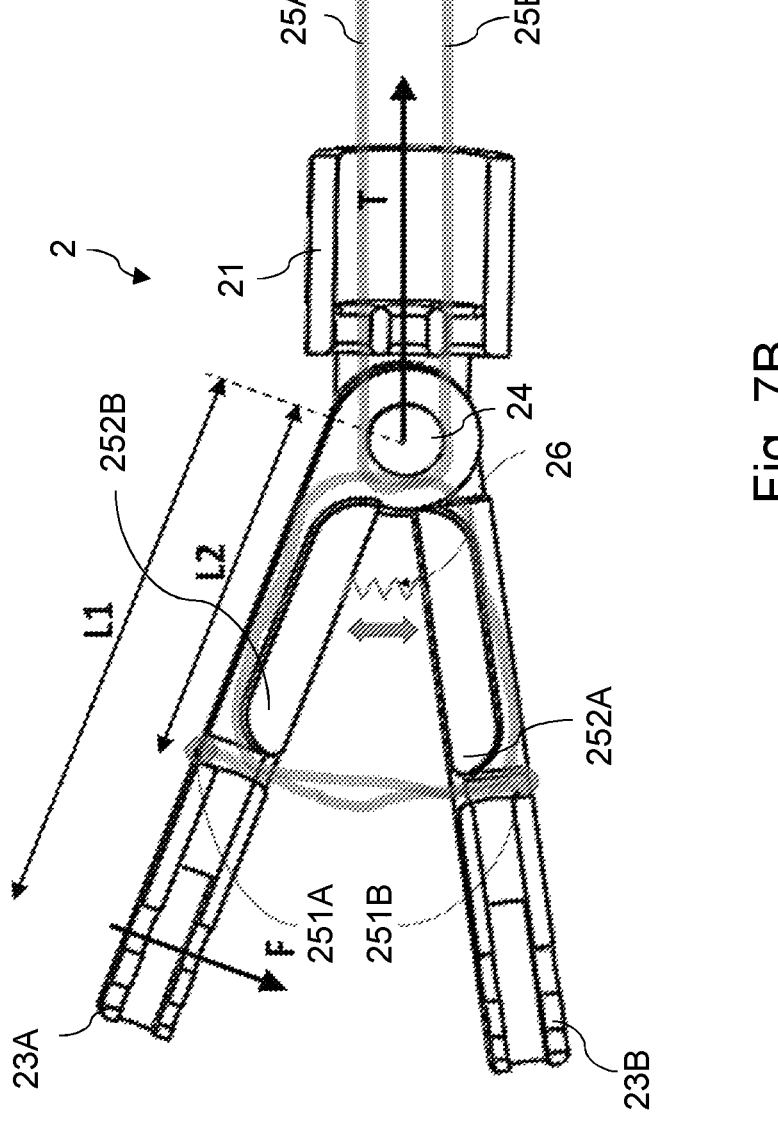

FIGS. 7A and 7B are schematic illustrations of a mechanism for controlling the jaws of the suturing tool. The mechanism of FIGS. 7A and 7B may equally be used in a grasping tool 2 in which the needle 3 is omitted and the jaws 23A and 23B are used for grasping.

Figure 1A:
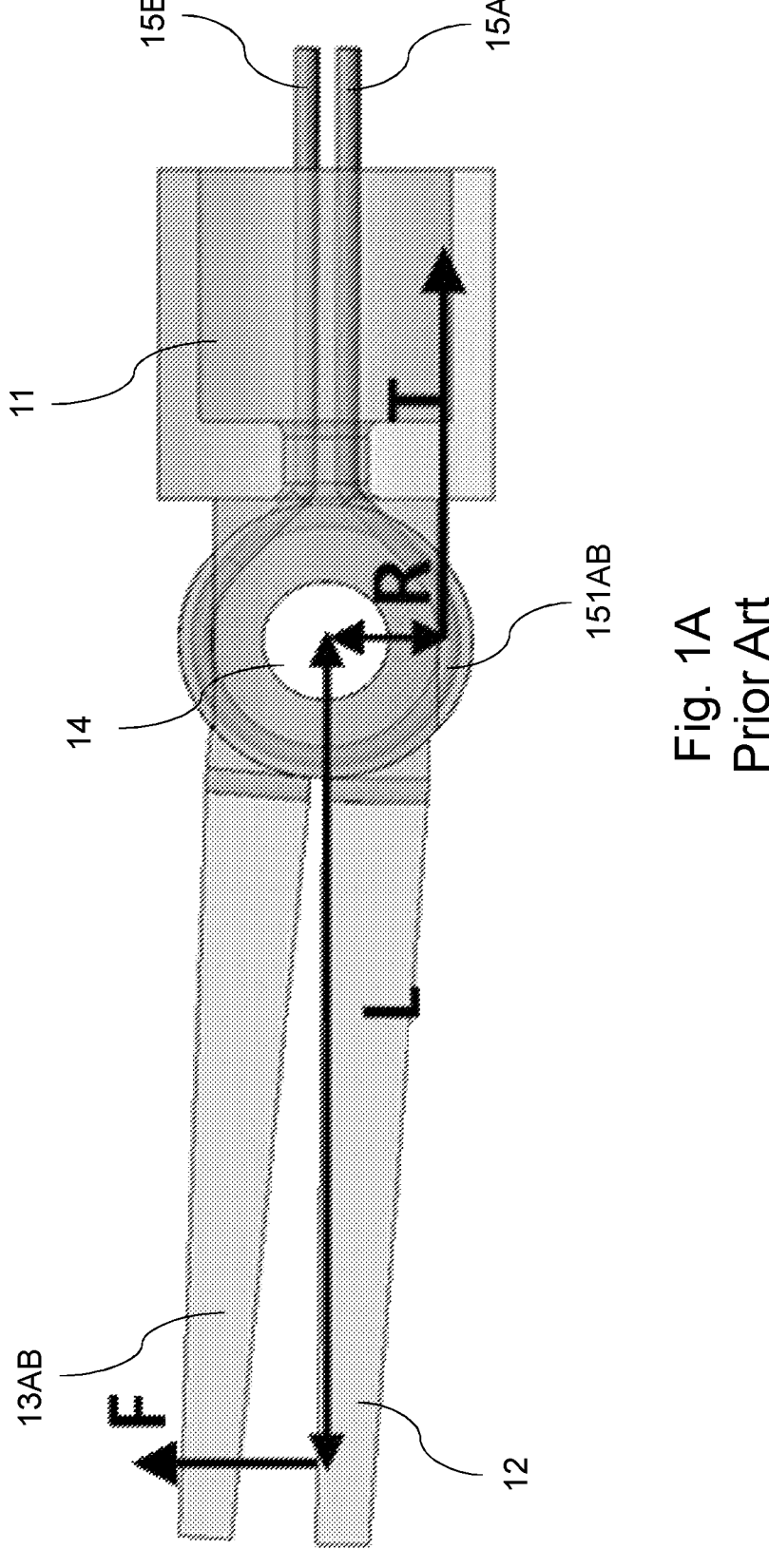
FIG. 1A is a schematic side view of a known grasping tool.
Figure 1B:
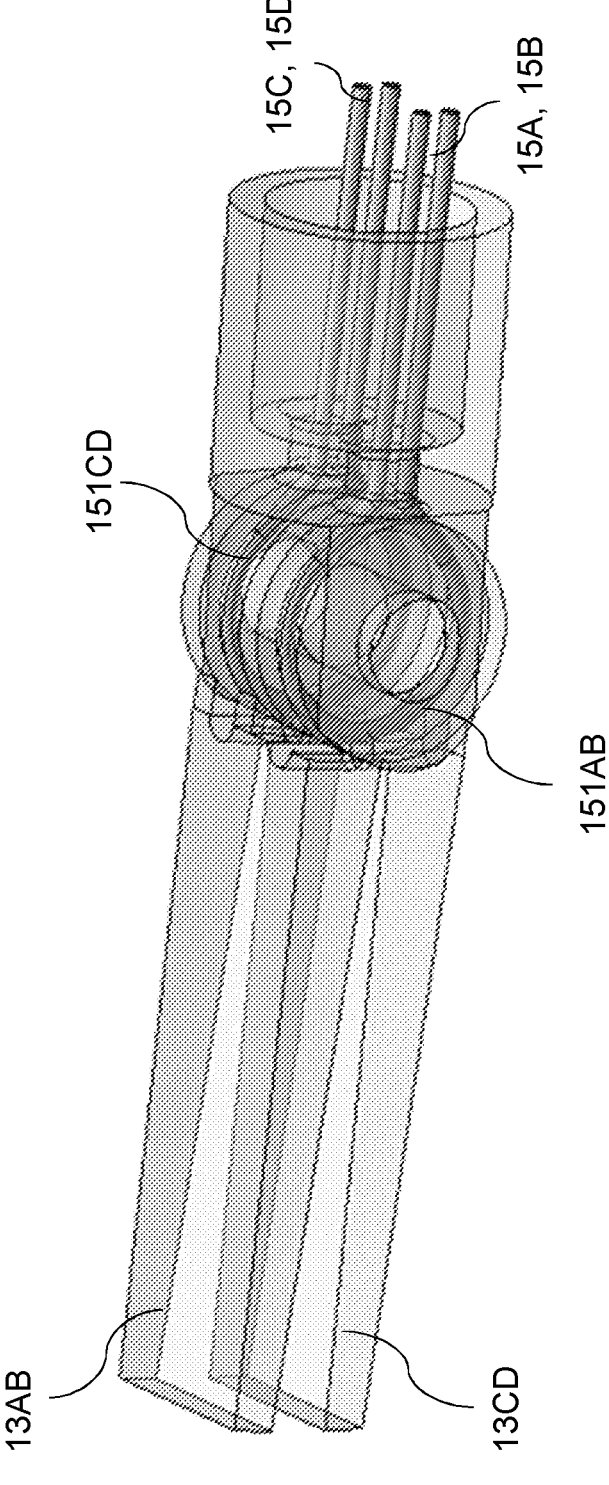
FIG. 1B is a schematic perspective view of another known grasping tool.
Figures 2A, 2B:
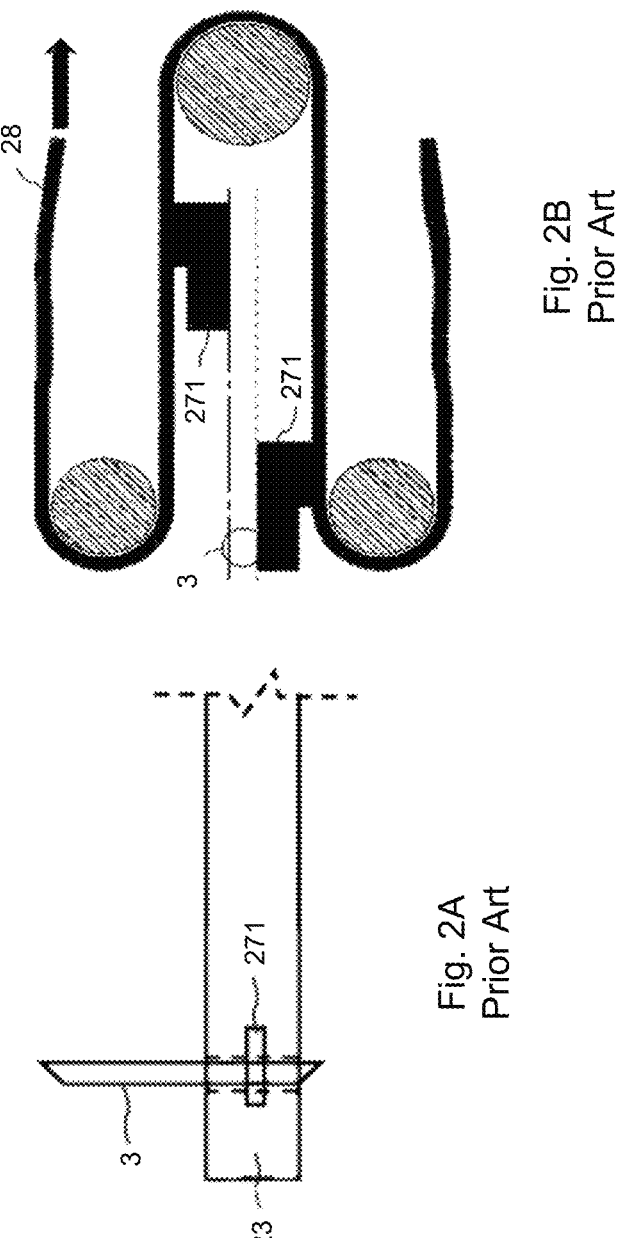
FIGS. 2A and 2B are schematic illustrations of a prior art suturing tool.

The mechanism of FIGS. 7A and 7B differs from the mechanism in known grasping tool 1 of FIG. 1B in how the moveable jaws are operated, but otherwise may be implemented in a similar manner to the known grasping tool 1. The support 21 and hinge 24 may be similar to the support 11 and hinge 14.

As shown in FIG. 7A, the first jaw 23A and second jaw 23B may each be moveable and comprise a first anchor 251A, 251B and a second pivot 252A, 252B which are configured to respectively anchor and pivot a jaw control tendon (not shown in FIG. 7A).

The first anchor 251A, 251B is located between a forward end and a backward end of each jaw. For example, each first anchor may be arranged midway along the jaw. The first anchor 251A, 251B is a point at which an end of a tendon is secured, for example by clamping or gluing. In some examples the first anchor 251A, 251B may be replaced with a first pivot at the same position, and the tendon may extend further past the first pivot to a separate anchor.

The second pivot 252A, 252B is also located between the forward end and the backward end of each jaw. For example the second pivot may be arranged adjacent to the first anchor 251B, 251A. The second pivot is a point at which a tendon is redirected. Each second pivot may for example comprise a pulley.

Either of the first anchor and the second pivot may be arranged closer to the backward end of each jaw. The arrangement of the first anchor and second pivot is preferably the same on both jaws to provide a symmetrical mechanism.

Additionally, a jaw biasing element 26 (such as a spring) may be arranged between the pair of jaws. A natural position of the jaw biasing element 26 may be configured to bias the pair of jaws to either an open position where there is significant space between the pair of jaws or a closed position where the jaws are close together.

In the grasping or suturing tool of FIG. 7A, the jaw biasing element 26 is configured to bias the pair of jaws to the open position. This may be preferred for a grasping tool because the force to open the pair of jaws is often lower than the maximum closing force required for grasping, and the controllable tendons may be capable of delivering a greater maximum force than the biasing element.

The jaw biasing element 26 may for example be integrated with the hinge 24 using a torsion spring. In some embodiments, the grasping or suturing tool may incorporate more than one jaw biasing element. For example, the tool may comprise a separate jaw biasing element configured to bias the position of a jaw relative to the support 11.

FIG. 7B illustrates the suturing or grasping tool 2 with jaw control tendons 25A and 25B in place.

A first jaw control tendon 25A is anchored to the first jaw 23A at the first anchor 251A, and extends from the first anchor 251A around the second pivot 252A of the second jaw 23B, and then through the support 21 to a control end of the tendon 25A. With this configuration tension in the first jaw control tendon 25A pulls the first anchor 251A of the first jaw 23A towards the second pivot 252A of the second jaw 23B.

Similarly, a second jaw control tendon 25B is anchored to the second jaw 23B at the first anchor 251B, and extends from the first anchor 251B around the second pivot 252B of the first jaw 23A, and then through the support 21 to a control end of the tendon 25B. With this configuration, tension in the second jaw control tendon 25B pulls the first anchor 251B of the second jaw 23B towards the second pivot 252B of the first jaw 23A.

As shown in FIG. 7B, each jaw control tendon 25A, 25B may also extend around a pulley surface of the hinge 24. This configuration simplifies the feed of the jaw control tendon backward through the probe towards the proximal end where the tendons are controlled.

As also shown in FIG. 7B, the second pivot may comprise an entrance to a channel extending along the respective jaw. For example, the jaw control tendon may be contained within the jaw between the second pivot and the hinge 14.

A maximum force F applied between the forward ends of the jaws 23A, 23B is dependent upon a length L1 of the jaws between the backward end and the forward end, a length L2 of the jaws between the backward end and the second pivot, and a maximum tension applied in the jaw control tendon. The force also depends on the angle between the jaw control tendon and the jaw as the jaw control tendon extends between the first anchor and the second pivot—this angle changes as the jaws open and close. The length L2 is typically greater than the radius R shown in FIG. 1A, meaning that the maximum force F is greater for the tool 2 than for the known grasping tool 1.

In some embodiments of a suturing tool, the jaw control tendons 25A, 25B may be connected to or combined with the needle control tendons 28A, 28B, such that pulling on one tendon can control both the open or closed jaw state and the open or closed lock state of each needle holder. Preferably in such embodiments the force required to move the jaws is lower than the force required to control the needle holders, such that the needle holders are only operated when the jaws are in the closed jaw position.

FIGS. 8A to 8E illustrate motion of the jaws 23A, 23B relative to the support 21, which can be controlled using the jaw control tendons 25A, 25B.

Figures 8A, 8B:
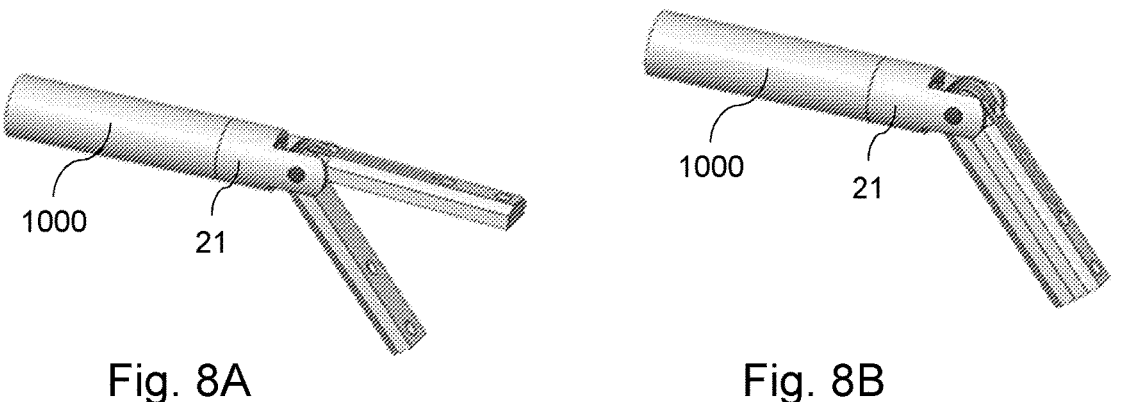
FIGS. 8A to 8E are schematic illustrations of the jaws of the suturing tool or the grasping tool in different positions.

When the first jaw control tendon 25A is tensioned and second jaw control tendon 25B is relaxed, the jaw biasing element 26 maintains the pair of jaws in the open jaw position, but the tension in the first jaw control tendon 25A rotates the pair of jaws as a whole around the hinge 24 in a positive rotation direction, as shown in FIG. 8A. If the pair of jaws reaches a limit of rotation motion, tension in the first jaw control tendon 25A may overcome a force provided by the jaw biasing element 26 and move the pair of jaws to the closed jaw position, as shown in FIG. 8B.

Figures 8C, 8D:
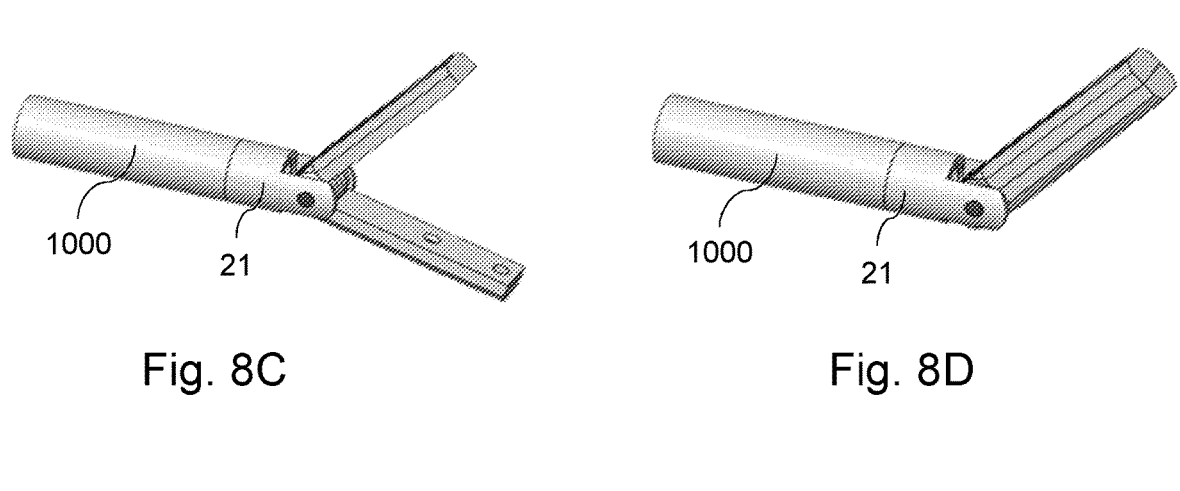

Similarly, when the second jaw control tendon 25B is tensioned and first jaw control tendon 25A is relaxed, the jaw biasing element 26 maintains the pair of jaws in the open jaw position, but the tension in the second jaw control tendon 25B rotates the pair of jaws as a whole around the hinge 24 in a negative rotation direction, as shown in FIG. 8C. If the pair of jaws reaches a limit of rotation motion, tension in the second jaw control tendon 25B may overcome a force provided by the jaw biasing element 26 and move the pair of jaws to the closed jaw position, as shown in FIG. 8D.

Figure 8E:
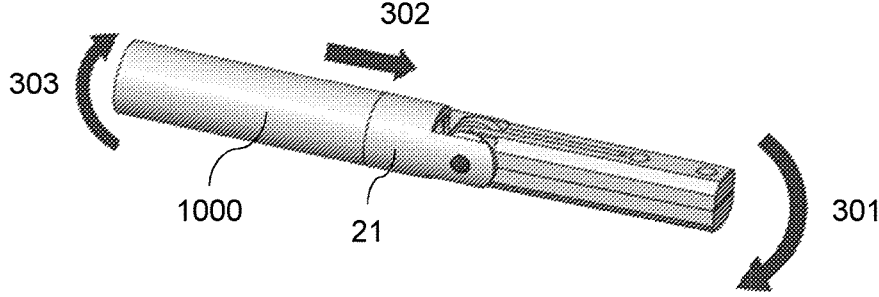

If the first and second jaw control tendons 25A, 25B are tensioned equally, the combined tension overcomes the force provided by the jaw biasing element 26 and moves the pair of jaws to the closed jaw position, without overall rotation of the pair of jaws, as shown in FIG. 8E.

FIG. 8E also shows arrows illustrating further motion of the suturing or grasping tool 2 which can be controlled separately. The arrow 301 illustrates rotation motion as described above with reference to FIGS. 8A to 8D. The arrow 302 illustrates motion along an axis of the distal end of the probe 1000 to which the support 21 is connected. This axial motion may be controlled by moving the probe. The arrow 303 illustrates rotation motion around the axis of the distal end of the probe 1000 to which the support 21 is connected. This rotation motion around the axis may be controlled by rotating the probe. Alternatively the motions 302, 303 may also be controlled by dividing the support 21 into two sections configured for relative motion, to provide complete control of motion of the suturing or grasping tool relative to the probe.

In embodiments where overall rotation of the jaw pair is not required (such as when the tool is used for grasping or suturing objects directly ahead of the tool), the jaw control tendons 25A, 25B may be joined together after they extend past the second pivots 252A, 252B, so that only one jaw control tendon takes up space in an internal channel of the probe.

Additionally, in some embodiments, one of the jaws 23B may be fixed relative to the support 21, or may be an extension of the support 21. In this case, the second jaw control tendon 25B and the associated anchors and pivots would be omitted.

Figures 9A, 9B:
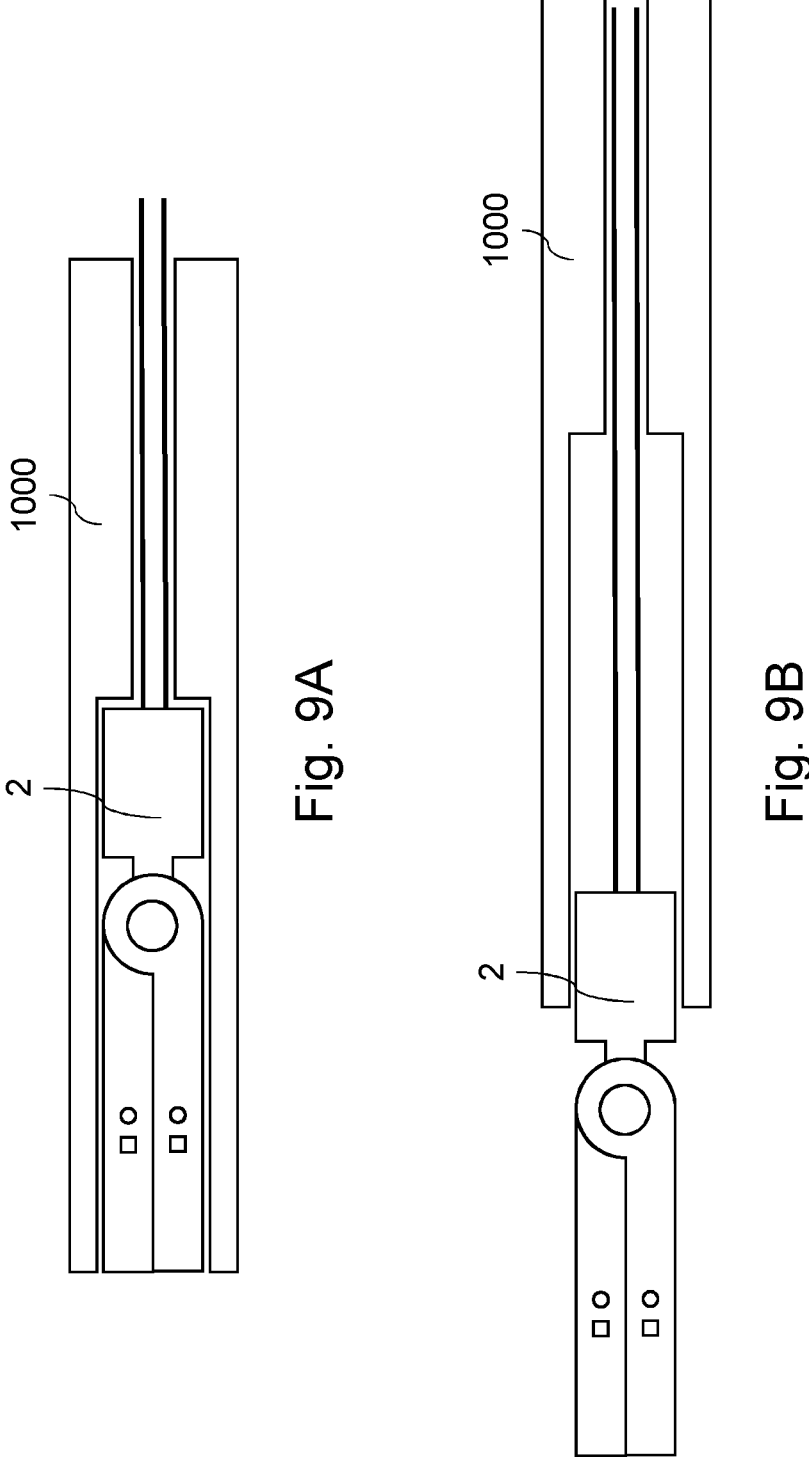
FIGS. 9A and 9B are schematic cross-section illustrations of a probe system comprising the suturing tool or the grasping tool.

The above described suturing or grasping tool can be deployed using known techniques for providing a tool at a distal end of a long probe, for example as illustrated in FIGS. 9A and 9B. FIGS. 9A and 9B are schematic cross-section illustrations of a probe system comprising the suturing or grasping tool.

As shown in FIG. 9A, the suturing or grasping tool 2 may be stored in an internal storage channel of the probe 1000, so that the probe can have a simple end shape while it is manoeuvred through a patient. Once the probe 1000 is in position, the suturing or grasping tool 2 may be deployed at the distal end of the probe 1000, as shown in FIG. 9B.

Alternatively, the suturing or grasping tool 2 may be attached to the distal end of the probe 1000, so that there is no need to move the suturing or grasping tool 2 relative to the probe 1000.

FIGS. 10A to 10D are schematic illustrations of the jaw biasing element 26 of the suturing or grasping tool in another embodiment. The alternative embodiment is largely the same as previously described, but includes the biasing element with a specific configuration as explained below.

A natural position of the jaw biasing element 26 may be configured to bias the pair of jaws to either an open position where there is significant space between the pair of jaws or a closed position where the jaws are close together.

Preferably, the jaw biasing element 26 is configured to bias the pair of jaws to the open position. This is preferred because the force to open the pair of jaws is often lower than a required maximum closing force (for example a force required to drive the needle through native tissue), and the jaw control tendons may be capable of delivering a greater maximum force than the jaw biasing element.

Figures 10A, 10B, 10C, 10D:
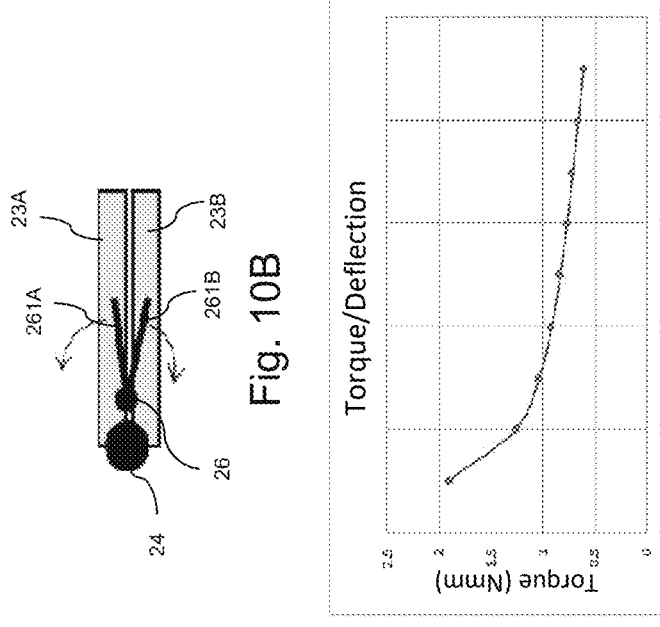
FIGS. 10A to 10D are schematic illustrations of the suturing tool in a case where the jaws are biased using a torsion spring.

As shown in FIG. 10A, the jaw biasing element 26 is a torsion spring having a centre that is offset from the hinge 24. More specifically, the centre of the torsion spring is offset so that it is located between the jaws, between their backward and forward ends. A connector 261A, 261B connects the jaw biasing element 26 to each jaw 23A, 23B.

With this configuration, a torque provided by the torsion spring 26 increases as it moves away from its natural shape. In this example, the natural shape of the torsion spring 26 corresponds to the open position of the jaws, so the torque increases as the jaws move from the open to the closed position.

On the other hand, an angle θ between the connectors 261A, 261B and the jaws 23A, 23B changes as the jaws open and close. As shown in FIG. 10B, the angle θ is relatively close to parallel (and too small to label) when the jaws are in the closed position. On the other hand, as shown in FIG. 10C, the angle θ is relatively close to perpendicular when the jaws are in the open position. The torque force is applied to the jaws in a direction perpendicular to the connectors 261A, 261B, so the torque is most directly applied to the jaws to bias the jaws to the open position when the angle θ is parallel and least directly applied to the jaws to bias the jaws to the open position when the angle θ is perpendicular.

The combination of these factors means that a force required to close the jaws from the open position to the closed position against the biasing element 26 is amplified in the closed position relative to the open position. FIG. 10D is a graph illustrating this force. In FIG. 10D, the x axis indicates an angle between the connectors 261A, 261B, meaning that lower angles correspond to the closed position and greater angles correspond to the open position. Additionally, the y axis indicates the force applied to the jaws to bias the jaws to the open position.

In other embodiments, the jaw biasing element 26 may for example be integrated with the hinge 24 using a torsion spring. In some embodiments, the tool may incorporate more than one jaw biasing element. For example, the tool may comprise a separate jaw biasing element configured to bias the position of a jaw relative to the support 21.

Figure 11:
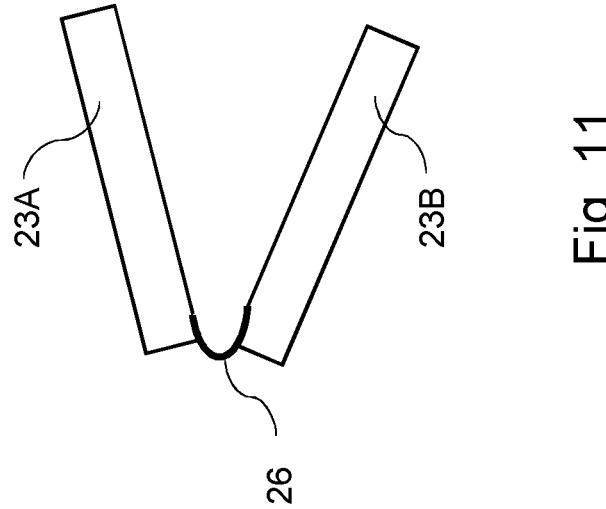
FIG. 11 is a schematic illustration of a suturing tool or grasping tool having an alternative jaw biasing element.

FIG. 11 is a schematic illustration of an alternative jaw biasing element 26. More specifically, in addition to or instead of a torsion spring, the jaw biasing element 26 comprises a resilient bending portion of each jaw 23A, 23B. With this configuration, the jaws can bend such that the forward ends of the jaws approach each other when the jaws move from the open to the closed jaw position, without the jaws necessarily approaching each other along their entire length.

As shown in FIG. 11, each jaw may comprise a rigid portion 23A, 23B and a resilient bending portion 26. More specifically, in the example of FIG. 11, the jaws are connected together using a spring element. In other examples, the jaws 23A, 23B may be resilient along their whole length.

The spring element may be included as a living hinge, in addition to or as a replacement of the pivoting hinge 24 described above for the suturing or grasping tool 2. As a result, the pair of jaws can be formed as one part with a living hinge. Furthermore, even if the living hinge is not resilient (i.e. a separate resilient element is used as in the above-described examples), such a living hinge may be used to replace the pivoting hinge 24.

Figure 12:
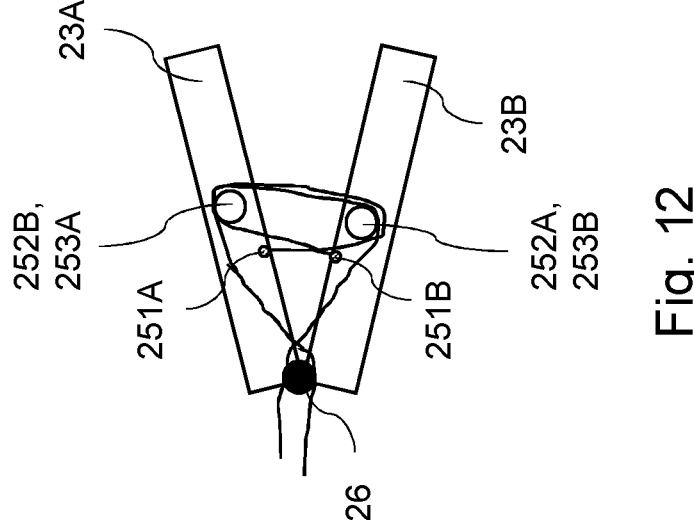
FIG. 12 is a schematic illustration of a suturing tool or grasping tool having an alternative tendon configuration for controlling the jaws.

FIG. 12 is a schematic illustration of an alternative jaw control tendon configuration for the suturing or grasping tool.

In FIG. 12, each jaw control tendon 25A, 25B extends between pivots/anchors of the opposing jaws 23A, 23B more than once, in order to increase the maximum closing force.

More specifically, each jaw 23A, 23B further comprises a third pivot 253A, 253B arranged between the forward end and the backward end of the jaw. Each jaw control tendon 25A, 25B extends around the third pivot 253A, 253B of one jaw 23A, 23B between extending around the second pivot 252A, 252B of the other jaw 23B, 23A and extending through the support 11. In some examples, the second pivots and third pivots may be the same features of each jaw, as shown in FIG. 12, although the second and third pivots may also be located at different positions along each jaw.

This principle can be extended further by arranging the jaw control tendons 25A, 25B to extend around the second pivot and/or third pivot more than once, or by adding additional pivots.

The invention claimed is:

1. A suturing tool for an endoscope or a laparoscope, the tool comprising:

a symmetric suturing needle comprising a point at each end of the needle; and a pair of jaws for suturing a target object between the jaws, each jaw comprising a needle holder for holding the suturing needle, the pair of jaws being configured to move between an open jaw position and a closed jaw position, wherein each needle holder comprises a moveable locking element configured to move between a closed lock position in which the suturing needle is held by the needle holder and an open lock position at which the suturing needle is released by the needle holder, and each needle holder further comprises a resilient control mechanism configured to switch the locking element between the closed lock position and the open lock position.

2. A suturing tool according to claim 1, wherein the jaws have opposite configurations of the control mechanism such that, when the locking element of one jaw is in the open lock position, the locking element of the other jaw is in the closed lock position.

3. A suturing tool according to claim 1, wherein the suturing needle comprises an engagement element adjacent to each end, the engagement element being adapted to engage with the locking element of a needle holder.

4. A suturing tool according to claim 1, wherein the control mechanism comprises a biasing element configured to bias the locking element toward one of the closed lock position and the open lock position, and a needle control tendon configured to move the locking element to the other of the closed lock position and the open lock position.

5. A suturing tool according to claim 1, wherein the control mechanism comprises a bistable latch mechanism configured to alternately switch the locking element between the open lock position and the closed lock position, and a latch trigger for triggering the latch mechanism.

6. A suturing tool according to claim 5, wherein the latch trigger is a needle control tendon.

7. A suturing tool according to claim 5, wherein the latch trigger is a pressure trigger configured to respond to a pressure applied to the needle by the pair of jaws.

8. A suturing tool according to claim 1, wherein the control mechanism comprises a needle control tendon that has a split distal end connected to the locking elements, and has a single proximal end.

9. A suturing tool according to claim 8, wherein the control mechanism comprises a needle control tendon that is also a jaw control tendon configured to move the pair of jaws between the open jaw position and the closed jaw position.

* * * * *